(12) United States Patent
McClanahan

(10) Patent No.: US 12,185,748 B2
(45) Date of Patent: Jan. 7, 2025

(54) BEADED TOBACCO MATERIAL AND RELATED METHOD OF MANUFACTURE

(71) Applicant: NICOVENTURES TRADING LIMITED, London (GB)

(72) Inventor: David Neil McClanahan, Winston-Salem, NC (US)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 18/207,931

(22) Filed: Jun. 9, 2023

(65) Prior Publication Data

US 2023/0329315 A1    Oct. 19, 2023

Related U.S. Application Data

(62) Division of application No. 16/798,638, filed on Feb. 24, 2020, now Pat. No. 11,712,059.

(51) Int. Cl.
| | | |
|---|---|---|
| *A24B 13/00* | (2006.01) | |
| *A24B 15/28* | (2006.01) | |
| *A24B 15/40* | (2006.01) | |
| *A61K 9/48* | (2006.01) | |
| *A61K 31/465* | (2006.01) | |

(52) U.S. Cl.
CPC ............ *A24B 13/00* (2013.01); *A24B 15/287* (2013.01); *A24B 15/403* (2013.01); *A61K 9/48* (2013.01); *A61K 31/465* (2013.01)

(58) Field of Classification Search
CPC ..... A24B 13/00; A24B 15/287; A24B 15/403; A61K 9/48; A61K 31/465
See application file for complete search history.

(56) References Cited

U.S. PATENT DOCUMENTS

| | | |
|---|---|---|
| 3,860,012 A | 1/1975 | Selke |
| 3,894,544 A | 7/1975 | Egri |
| 4,079,742 A | 3/1978 | Rainer et al. |
| 4,646,764 A | 3/1987 | Young et al. |
| 4,674,519 A | 3/1987 | Keritsis et al. |
| 4,793,365 A | 12/1988 | Sensabaugh et al. |
| 4,807,809 A | 2/1989 | Pryor et al. |
| 4,848,374 A | 7/1989 | Chard et al. |
| 4,924,887 A | 5/1990 | Raker et al. |
| 4,947,874 A | 8/1990 | Brooks et al. |
| 5,025,814 A | 6/1991 | Raker et al. |
| 5,042,509 A | 8/1991 | Banerjee et al. |
| 5,101,839 A | 4/1992 | Jakob et al. |
| 5,105,831 A | 4/1992 | Banerjee et al. |
| 5,159,942 A | 11/1992 | Brinkley et al. |
| 5,203,355 A | 4/1993 | Clearman et al. |
| 5,369,723 A | 11/1994 | Counts et al. |
| 5,396,911 A | 3/1995 | Casey, III et al. |
| 5,501,237 A | 3/1996 | Young et al. |
| 5,598,868 A | 2/1997 | Jakob et al. |
| 5,666,977 A | 9/1997 | Higgins et al. |
| 5,724,998 A | 3/1998 | Gellatly et al. |
| 5,819,751 A | 10/1998 | Barnes et al. |
| 7,032,601 B2 | 4/2006 | Atchley et al. |
| 7,428,905 B2 | 9/2008 | Mua |
| 7,647,932 B2 | 1/2010 | Cantrell et al. |
| 7,950,399 B2 | 5/2011 | Winterson et al. |
| 7,980,251 B2 | 7/2011 | Winterson et al. |
| 8,079,371 B2 | 12/2011 | Robinson et al. |
| 8,124,147 B2 | 2/2012 | Cheng et al. |
| 8,336,557 B2 | 12/2012 | Kumar et al. |
| 8,402,976 B2 | 3/2013 | Fernando et al. |
| 8,469,036 B2 | 6/2013 | Williams et al. |
| 8,469,037 B2 | 6/2013 | Liu et al. |
| 8,528,569 B1 | 9/2013 | Newton |
| 8,529,914 B2 | 9/2013 | Fuisz et al. |
| 8,613,285 B2 | 12/2013 | Fuisz |
| 8,627,828 B2 | 1/2014 | Strickland et al. |
| 8,747,562 B2 | 6/2014 | Mishra et al. |
| 8,846,075 B2 | 9/2014 | Jonsson et al. |
| 8,863,755 B2 | 10/2014 | Zhuang et al. |
| 8,978,661 B2 | 3/2015 | Atchley et al. |
| 8,992,974 B2 | 3/2015 | McCarty |
| 9,044,049 B2 | 6/2015 | Winterson et al. |
| 9,066,540 B2 | 6/2015 | Atchley et al. |
| 9,078,473 B2 | 7/2015 | Worm et al. |
| 9,149,072 B2 | 10/2015 | Conner et al. |
| 9,161,567 B2 | 10/2015 | Shikata et al. |

(Continued)

FOREIGN PATENT DOCUMENTS

| | | |
|---|---|---|
| CN | 104856215 A | 8/2015 |
| CN | 103750535 A | 12/2015 |

(Continued)

OTHER PUBLICATIONS

"Modified Cross-Section Viscose Fibre: Galaxy VY—Trilobal Cellulosic Fibre," <htlps://web.archive.org/,veb/20160519070915/http://www.kelheim-fibres.com:80/pdf/TDS_Galaxy_VY_0814.pdf>, p. 1.

*Primary Examiner* — Shirley V Gembeh
(74) *Attorney, Agent, or Firm* — WOMBLE BOND DICKINSON (US) LLP

(57) ABSTRACT

The disclosure provides a product including a plurality of beads configured for oral use, the plurality of beads containing bleached plant material, a filler, a binder, water, and at least one flavoring agent, active ingredient, or a combination thereof. Further provided are pouched products including the plurality of beads, and a process for preparing the beads.

15 Claims, 1 Drawing Sheet

(56) References Cited

U.S. PATENT DOCUMENTS

| | | |
|---|---|---|
| 9,161,908 B2 | 10/2015 | Nilsson |
| 9,167,835 B2 | 10/2015 | Sengupta et al. |
| 9,185,931 B2 | 11/2015 | Gao et al. |
| 9,237,768 B2 | 1/2016 | Carroll et al. |
| 9,345,268 B2 | 5/2016 | Stone et al. |
| 9,358,296 B2 | 6/2016 | McCarty |
| 9,402,414 B2 | 8/2016 | Griscik et al. |
| 9,414,624 B2 | 8/2016 | Carroll et al. |
| 9,462,827 B2 | 10/2016 | Carroll et al. |
| 9,468,233 B2 | 10/2016 | Macko et al. |
| 9,521,864 B2 | 12/2016 | Gao et al. |
| 9,693,582 B2 | 7/2017 | Carroll et al. |
| 9,788,571 B2 | 10/2017 | Conner et al. |
| 9,848,634 B2 | 12/2017 | Fuisz |
| 9,854,830 B2 | 1/2018 | Gao et al. |
| 9,854,831 B2 | 1/2018 | Gao et al. |
| 9,884,015 B2 | 2/2018 | Gao et al. |
| 9,925,145 B2 | 3/2018 | Hübinette et al. |
| 9,930,909 B2 | 4/2018 | Gao et al. |
| 9,974,334 B2 | 5/2018 | Dooly et al. |
| 9,986,756 B2 | 6/2018 | Gao et al. |
| 9,999,243 B2 | 6/2018 | Gao et al. |
| 10,039,309 B2 | 8/2018 | Carroll et al. |
| 10,104,912 B2 | 10/2018 | Sur |
| 10,105,320 B2 | 10/2018 | Gao et al. |
| 10,130,120 B2 | 11/2018 | Mishra et al. |
| 10,172,810 B2 | 1/2019 | McCarty |
| 10,244,786 B2 | 4/2019 | Gao et al. |
| 10,292,431 B2 | 5/2019 | White |
| 10,315,889 B2 | 6/2019 | Kreischer et al. |
| 10,321,707 B2 | 6/2019 | Klipfel et al. |
| 10,327,473 B2 | 6/2019 | Mironov |
| 10,334,873 B2 | 7/2019 | Mishra et al. |
| 10,405,572 B2 | 9/2019 | Batista |
| 10,412,989 B2 | 9/2019 | Klipfel et al. |
| 10,420,365 B2 | 9/2019 | Klipfel et al. |
| 10,440,995 B2 | 10/2019 | Sebastian et al. |
| 10,609,949 B2 | 4/2020 | Hodin et al. |
| 10,647,459 B2 | 5/2020 | Persson |
| 10,750,773 B2 | 8/2020 | Yang et al. |
| 10,791,756 B2 | 10/2020 | Zuchuat et al. |
| 10,798,969 B2 | 10/2020 | Hejazi et al. |
| 2004/0129280 A1 | 7/2004 | Woodson et al. |
| 2004/0226568 A1 | 11/2004 | Takeuchi et al. |
| 2008/0017203 A1 | 1/2008 | Fagg et al. |
| 2008/0029110 A1* | 2/2008 | Dube ............... A24B 13/00 131/274 |
| 2008/0308115 A1 | 12/2008 | Zimmerman |
| 2009/0025738 A1 | 1/2009 | Mua et al. |
| 2010/0300464 A1 | 12/2010 | Gee et al. |
| 2011/0232657 A1 | 9/2011 | Karles et al. |
| 2012/0138073 A1 | 6/2012 | Cantrell et al. |
| 2013/0206150 A1 | 8/2013 | Duggins et al. |
| 2013/0206153 A1 | 8/2013 | Beeson et al. |
| 2013/0251779 A1 | 9/2013 | Svandal et al. |
| 2014/0305448 A1 | 10/2014 | Zuber et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0150302 A1 | 6/2015 | Metrangolo et al. |
| 2015/0157052 A1 | 6/2015 | Ademe et al. |
| 2015/0313283 A1 | 11/2015 | Collett et al. |
| 2017/0055576 A1 | 3/2017 | Beeson et al. |
| 2017/0065000 A1 | 3/2017 | Sears et al. |
| 2017/0071250 A1 | 3/2017 | Mironov et al. |
| 2017/0280764 A1 | 10/2017 | Sahlén et al. |
| 2017/0318858 A1 | 11/2017 | Hodin et al. |
| 2018/0140007 A1 | 5/2018 | Aspgren et al. |
| 2018/0153211 A1 | 6/2018 | Persson |
| 2018/0237273 A1 | 8/2018 | Kreischer et al. |
| 2018/0255826 A1 | 9/2018 | Persson et al. |
| 2019/0183177 A1 | 6/2019 | Hubbard et al. |
| 2019/0255035 A1 | 8/2019 | Bruun |
| 2019/0291900 A1 | 9/2019 | Persson et al. |
| 2020/0093182 A1 | 3/2020 | Monsalud et al. |
| 2020/0154784 A1 | 5/2020 | Sebastian et al. |
| 2020/0281249 A1 | 9/2020 | Sebastian et al. |
| 2021/0169785 A1* | 6/2021 | Holton, Jr. ......... A61K 36/258 |

FOREIGN PATENT DOCUMENTS

| | | |
|---|---|---|
| CN | 105747266 A | 7/2016 |
| CN | 105919152 A | 9/2016 |
| CN | 106235376 A | 12/2016 |
| CN | 107616540 A | 1/2018 |
| CN | 107616541 A | 1/2018 |
| CN | 105768191 A | 3/2018 |
| CN | 107927891 A | 4/2018 |
| CN | 108143004 A | 6/2018 |
| CN | 108208917 A | 6/2018 |
| CN | 108323793 A | 7/2018 |
| CN | 108451001 A | 8/2018 |
| CN | 108451054 A | 8/2018 |
| CN | 108497544 A | 9/2018 |
| CN | 107259632 A | 10/2018 |
| CN | 107307466 A | 10/2018 |
| CN | 107319627 A | 10/2018 |
| CN | 108652067 A | 10/2018 |
| CN | 106368069 A | 2/2019 |
| EP | 2832244 | 2/2015 |
| GB | 2534213 A | 2/2018 |
| WO | WO 1997/032490 | 9/1997 |
| WO | WO 1997/032492 | 9/1997 |
| WO | WO 1999/063844 | 12/1999 |
| WO | WO 2006/090290 | 8/2006 |
| WO | WO 2010/113702 | 10/2010 |
| WO | WO 2011/101164 | 8/2011 |
| WO | WO 2012/133289 | 10/2012 |
| WO | WO 2013/178769 | 12/2013 |
| WO | WO 2015/055567 | 4/2015 |
| WO | WO 2015/082652 | 6/2015 |
| WO | WO 2015/176898 | 11/2015 |
| WO | WO 2015/177265 | 11/2015 |
| WO | WO 2016/050471 | 4/2016 |
| WO | WO 2016/090075 | 6/2016 |
| WO | WO 2016/156219 | 10/2016 |
| WO | WO 2016/156598 | 10/2016 |
| WO | WO 2016/162446 | 10/2016 |
| WO | WO 2017/041920 | 3/2017 |
| WO | WO 2017/051034 | 3/2017 |
| WO | WO 2017/068091 | 4/2017 |
| WO | WO 2017/068092 | 4/2017 |
| WO | WO 2017/068093 | 4/2017 |
| WO | WO 2017/068099 | 4/2017 |
| WO | WO 2017/077110 | 5/2017 |
| WO | WO 2017/077112 | 5/2017 |
| WO | WO 2017/108912 | 6/2017 |
| WO | WO 2018/033477 | 2/2018 |
| WO | WO 2018/162515 | 3/2018 |
| WO | WO 2018/172389 | 3/2018 |
| WO | WO 2018/122070 | 7/2018 |
| WO | WO 2018/152334 | 8/2018 |
| WO | WO 2018/197454 | 11/2018 |
| WO | WO 2018/215481 | 11/2018 |
| WO | WO 2019/036243 | 2/2019 |
| WO | WO 2019/105960 | 6/2019 |
| WO | WO 2019/115778 | 6/2019 |
| WO | WO 2019/162918 | 8/2019 |

\* cited by examiner

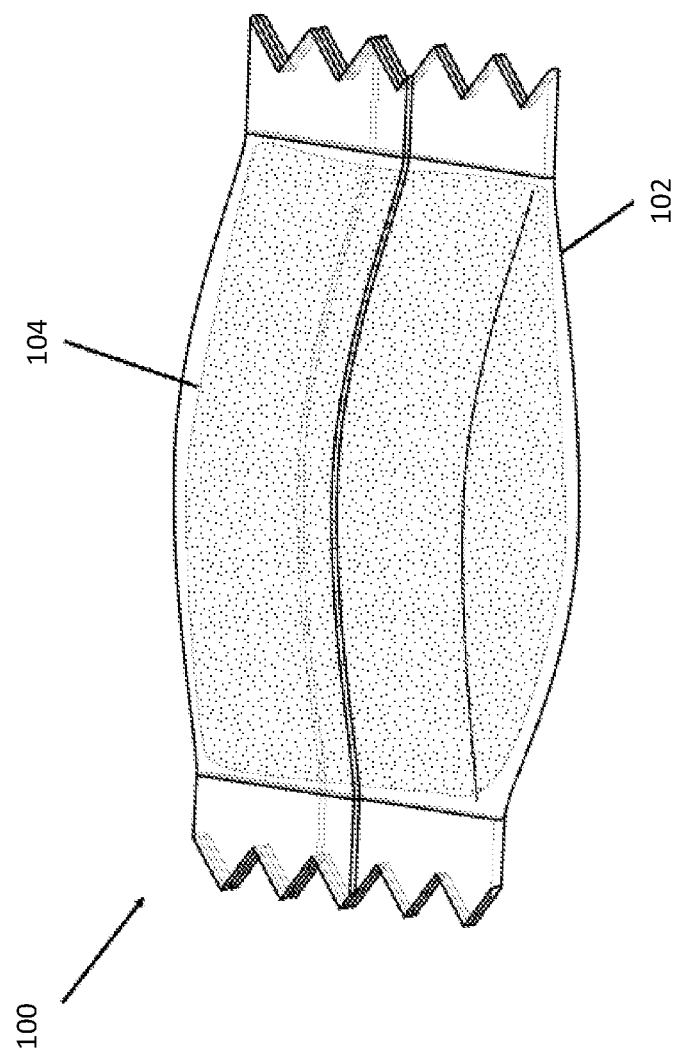

BEADED TOBACCO MATERIAL AND RELATED METHOD OF MANUFACTURE

CROSS-REFERENCE TO RELATED APPLICATIONS

This application is a divisional of U.S. patent application Ser. No. 16/798,638, filed on Feb. 24, 2020, the content of which is hereby incorporated by reference in its entirety

FIELD OF THE DISCLOSURE

The present disclosure relates to compositions intended for human use. The compositions are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; U.S. Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

All-white snus portions are growing in popularity, and offer a discrete and aesthetically pleasing alternative to traditional snus. Such modern "white" pouched products include a bleached tobacco or botanical material. It may be desirable to provide alternative forms of bleached plant material that may be incorporated into all-white snus portions and/or other oral products to provide certain desirable properties.

BRIEF SUMMARY

The present disclosure is generally directed to beads comprising a bleached plant material and processes for making such beads. Accordingly, in one aspect the disclosure provides a product comprising a plurality of beads configured for oral use, the plurality of beads comprising: from about 0.1 to about 80% by weight of a bleached plant material, based on the total weight of the beads; at least about 10% by weight of a filler, based on the total weight of the beads; at least about 0.25% by weight of a binder, based on the total weight of the beads; up to about 60% by weight of water, based on the total weight of the beads; and at least one flavoring agent, active ingredient, or a combination thereof.

In some embodiments, the plurality of beads comprises less than about 10%, less than about 8%, or less than about 6% by weight of the bleached plant material, based on the total weight of the beads. In some embodiments, the product comprises from about 0.1 to about 5% by weight of the bleached plant material, based on the total weight of the beads.

In some embodiments, the plurality of beads comprises from about 10-75% of the filler by weight, such as from about 10 to about 60%, about 20 to about 50%, or about 25 to about 45% by weight, based on the total weight of the beads.

In some embodiments, the plurality of beads comprises from about 1-5% binder by weight, based on the total weight of the beads.

In some embodiments, the plurality of beads comprises from about 5 to about 55%, from about 10 to about 50%, from about 20 to about 45%, or from about 25 to about 40% water by weight, based on the total weight of the beads. In some embodiments, the plurality of beads comprises from about 5 to about 25% water by weight, based on the total weight of the beads.

In some embodiments, the diameter of each of the beads is from about 1 mm to about 10 mm. In some embodiments, the diameter of each of the beads is from about 1 mm to about 5 mm.

In some embodiments, the bleached plant material has a particle size of from about 50 to about 1 mm.

In some embodiments, the bleached plant material comprises a tobacco material, a non-tobacco botanical material, or a combination thereof. In some embodiments, the bleached plant material consists of tobacco stems, stalks, roots, extracted fiber, or a combination thereof. In some embodiments, the bleached plant material comprises Rustica tobacco stems. In some embodiments, the bleached plant material consists of Rustica tobacco stems. In some embodiments, the beads are substantially free of tobacco material. In some embodiments, the beads are substantially free of unbleached tobacco material.

In some embodiments, the weight of the filler is greater than weight of the bleached plant material. In some embodiments, the weight of the filler is at least twice the weight of bleached plant material. In some embodiments, the weight of the filler is from about 2 to about 100, or from about 5 to about 50, or from about 10 to about 20 times the weight of bleached plant material.

In some embodiments, the binder is selected from the group consisting of alginates, cellulose ethers, gums, dextrans, carrageenan, and combinations thereof. In some embodiments, the binder is a cellulose ether selected from the group consisting of methylcellulose, hydroxyethyl cellulose, hydroxypropylcellulose (HPC), hydroxypropylmethylcellulose (HPMC), carboxymethylcellulose (CMC), and combinations thereof. In some embodiments, the binder is CMC.

In some embodiments, the active ingredient comprises one or more nicotine components, stimulants, amino acids, vitamins, antioxidants, cannabinoids, nutraceuticals, pharmaceutical agents, or a combination thereof. In some embodiments, the beads are substantially free of nicotine. In some embodiments, the active ingredient comprises a nicotine component. In some embodiments, the product further comprises one or more salts, one or more sweeteners, one or more humectants, or combinations thereof.

In some embodiments, a whiteness value of the beads is greater than about 40, when determined according to the Commission Internationale de l'Eclairage (CIE) model. In some embodiments, the whiteness value is from about 42 to about 60.

In some embodiments, the product is enclosed in a pouch to form a pouched product. In some embodiments, a whiteness value of the pouched product is greater than about 40, when determined according to the Commission Internationale de l'Eclairage (CIE) model. In some embodiments, the whiteness value is from about 42 to about 60.

In another aspect is provided a white product comprising a plurality of white beads configured for oral use, the plurality of white beads comprising: from about 0.1 to about 80% by weight of a bleached plant material, based on the total weight of the white beads; at least about 10% by weight of a filler, based on the total weight of the white beads; at least about 0.25% by weight of a binder, based on the total weight of the white beads; up to about 60% by weight of water, based on the total weight of the white beads; and at least one flavoring agent, active ingredient, or a combination thereof; and wherein a whiteness value of the white beads is greater than about 40, when determined according to the Commission Internationale de l'Eclairage (CIE) model.

In some embodiments, the white beads have a diameter of from about 1 mm to about 10 mm. In some embodiments, the white beads have a diameter of from about 1 mm to about 5 mm.

In another aspect is provided a process for preparing a product comprising a plurality of beads configured for oral use, the plurality of beads comprising a bleached plant material, a binder, a filler, water, and at least one flavoring agent, active ingredient, or a combination thereof, the process comprising: receiving a bleached plant material having a particle size of from about 50 µm to about 1 mm; adding water, a filler, a binder, and at least one flavoring agent, active ingredient, or a combination thereof, to the bleached plant material to form a mixture; granulating the mixture to form an agglomerate; extruding the agglomerate to form an extrudate; spheronizing the extrudate to form the beads; and optionally, drying the beads.

In some embodiments, the process further comprises grinding the bleached plant material to reduce the particle size prior to said adding. In some embodiments, the process further comprises adding one or more salts, one or more sweeteners, one or more humectants, or combinations thereof, to the bleached plant material prior to granulating. In some embodiments, the process further comprises enclosing the beads in a pouch to form a pouched product.

In some embodiments, the bleached plant material comprises a tobacco material, a non-tobacco botanical material, or a combination thereof. In some embodiments, the bleached plant material consists of tobacco stems, stalks, roots, extracted fiber, or a combination thereof. In some embodiments, the bleached plant material comprises Rustica tobacco stems. In some embodiments, the bleached plant material consists of Rustica tobacco stems. In some embodiments, the bleached plant material is substantially free of tobacco material. In some embodiments, the bleached plant material is substantially free of unbleached tobacco material.

In some embodiments, the binder is selected from the group consisting of alginates, cellulose ethers, gums, dextrans, carrageenan, and combinations thereof. In some embodiments, the binder is a cellulose ether selected from the group consisting of methylcellulose, hydroxyethyl cellulose, hydroxypropylcellulose (HPC), hydroxypropylmethylcellulose (HPMC), carboxymethylcellulose (CMC), and combinations thereof. In some embodiments, binder is CMC.

In some embodiments, the active ingredient comprises one or more nicotine components, stimulants, amino acids, vitamins, antioxidants, cannabinoids, nutraceuticals, pharmaceutical agents, or a combination thereof. In some embodiments, the active ingredient comprises a nicotine component. In some embodiments, the beads are substantially free of nicotine.

In some embodiments, the beads are from about 1 to about 10 mm in diameter. In some embodiments, the beads are from about 1 to about 5 mm in diameter.

The disclosure includes, without limitations, the following embodiments.

Embodiment 1: A product comprising a plurality of beads configured for oral use, the plurality of beads comprising: from about 0.1 to about 80% by weight of a bleached plant material, based on the total weight of the beads; at least about 10% by weight of a filler, based on the total weight of the beads; at least about 0.25% by weight of a binder, based on the total weight of the beads; up to about 60% by weight of water, based on the total weight of the beads; and at least one flavoring agent, active ingredient, or a combination thereof.

Embodiment 2: The product of the first embodiment, the plurality of beads comprising less than about 10%, less than about 8%, or less than about 6% by weight of the bleached plant material, based on the total weight of the beads.

Embodiment 3: The product of the first or second embodiment, the plurality of beads comprising from about 0.1 to about 5% by weight of the bleached plant material, based on the total weight of the beads.

Embodiment 4: The product of any one of embodiments 1 to 3, the plurality of beads comprising from about 10-75% of the filler by weight, such as from about 10 to about 60%, about 20 to about 50%, or about 25 to about 45% by weight, based on the total weight of the beads.

Embodiment 5: The product of any one of embodiments 1 to 4, the plurality of beads comprising from about 1-5% binder by weight, based on the total weight of the beads.

Embodiment 6: The product of any one of embodiments 1 to 5, the plurality of beads comprising from about 5 to about 55%, from about 10 to about 50%, from about 20 to about 45%, or from about 25 to about 40% water by weight, based on the total weight of the bead.

Embodiment 7: The product of any one of embodiments 1 to 6, the plurality of beads comprising from about 5 to about 25% water by weight, based on the total weight of the bead.

Embodiment 8: The product of any one of embodiments 1 to 7, wherein the diameter of the beads is from about 1 mm to about 10 mm, or from about 1 mm to about 5 mm.

Embodiment 9: The product of any one of embodiments 1 to 8, wherein the bleached plant material has a particle size of from about 50 µm to about 1 mm.

Embodiment 10: The product of any one of embodiments 1 to 9, wherein the bleached plant material comprises a tobacco material, a non-tobacco botanical material, or a combination thereof.

Embodiment 11: The product of any one of embodiments 1 to 10, wherein the bleached plant material consists of tobacco stems, tobacco stalks, tobacco roots, extracted tobacco fiber, or a combination thereof.

Embodiment 12: The product of any one of embodiments 1 to 11, wherein the bleached plant material comprises or consists of Rustica tobacco stems.

Embodiment 13: The beaded product of any one of embodiments 1 to 12, wherein the beads are substantially free of tobacco material.

Embodiment 14: The beaded product of any one of embodiments 1 to 13, wherein the beads are substantially free of unbleached tobacco material.

Embodiment 15: The product of any one of embodiments 1 to 14, wherein the weight of the filler is greater than the weight of the bleached plant material.

Embodiment 16: The product of any one of embodiments 1 to 15, wherein the weight of the filler is at least twice the weight of bleached plant material.

Embodiment 17: The product of any one of embodiments 1 to 16, wherein the weight of the filler is from about 2 to about 100, or from about 5 to about 50, or from about 10 to about 20 times the weight of bleached plant material.

Embodiment 18: The product of any one of embodiments 1 to 17, wherein the binder is selected from the group consisting of alginates, cellulose ethers, gums, dextrans, carrageenan, and combinations thereof.

Embodiment 19: The product of any one of embodiments 1 to 18, wherein the binder is a cellulose ether selected from the group consisting of methylcellulose, hydroxyethyl cellulose, hydroxypropylcellulose (HPC), hydroxypropylmethylcellulose (HPMC), carboxymethylcellulose (CMC), and combinations thereof.

Embodiment 20: The product of any one of embodiments 1 to 19, wherein the binder is CMC.

Embodiment 21: The product of any one of embodiments 1 to 20, wherein the active ingredient comprises one or more nicotine components, stimulants, amino acids, vitamins, antioxidants, cannabinoids, nutraceuticals, pharmaceutical agents, or a combination thereof.

Embodiment 22: The product of any one of embodiments 1 to 21, wherein the beads are substantially free of nicotine.

Embodiment 23: The product of any one of embodiments 1 to 22, wherein the active ingredient comprises a nicotine component.

Embodiment 24: The product of any one of embodiments 1 to 23, further comprising one or more salts, one or more sweeteners, one or more humectants, or combinations thereof.

Embodiment 25: The product of any one of embodiments 1 to 24, enclosed in a pouch to form a pouched product.

Embodiment 26: The product of any one of embodiments 1 to 25, wherein a whiteness value of the beads is greater than about 40, when determined according to the Commission Internationale de l'Eclairage (CIE) model.

Embodiment 27: The product of any one of embodiments 1 to 26, wherein a whiteness value of the pouched product is greater than about 40, when determined according to the Commission Internationale de l'Eclairage (CIE) model.

Embodiment 28: The product of any one of embodiments 1 to 27, wherein the whiteness value is from about 42 to about 60.

Embodiment 29: The product of any one of embodiments 1 to 28, wherein the whiteness value is from about 42 to about 60.

Embodiment 30: A white product comprising a plurality of white beads configured for oral use, the plurality of white beads comprising: from about 0.1 to about 80% by weight of a bleached plant material, based on the total weight of the white beads; at least about 10% by weight of a filler, based on the total weight of the white beads; at least about 0.25% by weight of a binder, based on the total weight of the white beads; up to about 60% by weight of water, based on the total weight of the white beads; and at least one flavoring agent, active ingredient, or a combination thereof and wherein a whiteness value of the white beads is greater than about 40, when determined according to the Commission Internationale de l'Eclairage (CIE) model.

Embodiment 31: The white product of embodiment 30, wherein the beads are from about 1 to about 10 mm in diameter, or from about 1 to about 5 mm in diameter.

Embodiment 32: A process for preparing a product comprising a plurality of beads configured for oral use, the plurality of beads comprising a bleached plant material, a binder, a filler, water, and at least one flavoring agent, active ingredient, or a combination thereof, the process comprising: receiving a bleached plant material having a particle size of from about 50 μm to about 1 mm; adding water, a filler, a binder, and at least one flavoring agent, active ingredient, or a combination thereof, to the bleached plant material to form a mixture; granulating the mixture to form an agglomerate; extruding the agglomerate to form an extrudate; spheronizing the extrudate to form beads; and optionally, drying the beads.

Embodiment 33: The process of embodiment 32, further comprising grinding the bleached plant material to reduce the particle size prior to said adding.

Embodiment 34: The process of embodiment 32 or 33, wherein the bleached plant material comprises a tobacco material, a non-tobacco botanical material, or a combination thereof.

Embodiment 35: The process of any one of embodiments 32 to 34, wherein the bleached plant material consists of tobacco stems, tobacco stalks, tobacco roots, extracted tobacco fiber, or a combination thereof.

Embodiment 36: The process of any one of embodiments 32 to 35, wherein the bleached plant material consists of Rustica tobacco stems.

Embodiment 37: The process of any one of embodiments 32 to 36, wherein the bleached plant material is substantially free of tobacco material.

Embodiment 38: The process of any one of embodiments 32 to 37, wherein the bleached plant material is substantially free of unbleached tobacco material.

Embodiment 39: The process of any one of embodiments 32 to 38, further comprising adding one or more salts, one or more sweeteners, one or more humectants, or combinations thereof, to the bleached plant material prior to granulating.

Embodiment 40: The process of any one of embodiments 32 to 39, wherein the binder is selected from the group consisting of alginates, cellulose ethers, gums, dextrans, carrageenan, and combinations thereof.

Embodiment 41: The process of any one of embodiments 32 to 40, wherein the binder is a cellulose ether selected from the group consisting of methylcellulose, hydroxyethyl cellulose, hydroxypropylcellulose (HPC), hydroxypropylmethylcellulose (HPMC), carboxymethylcellulose (CMC), and combinations thereof.

Embodiment 42: The process of any one of embodiments 32 to 41, wherein the binder is CMC.

Embodiment 43: The process of any one of embodiments 32 to 42, wherein the active ingredient comprises one or more nicotine components, stimulants, amino acids, vitamins, antioxidants, cannabinoids, nutraceuticals, pharmaceutical agents, or a combination thereof.

Embodiment 44: The process of any one of embodiments 32 to 43, wherein the active ingredient comprises a nicotine component.

Embodiment 45: The process of any one of embodiments 32 to 44, wherein the beads are substantially free of nicotine.

Embodiment 46: The process of any one of embodiments 32 to 45, wherein the beads are from about 1 to about 10 mm in diameter, or from about 1 to about 5 mm in diameter.

Embodiment 47: The process of any one of embodiments 32 to 46, further comprising enclosing the beads in a pouch to form a pouched product.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWING

Having thus described aspects of the disclosure in the foregoing general terms, reference will now be made to the accompanying drawing, which is not necessarily drawn to scale. The drawing is exemplary only, and should not be construed as limiting the disclosure.

The drawing is a perspective view of a pouched product according to an example embodiment of the present disclosure including a pouch or fleece at least partially filled with a plurality of beads of the present disclosure.

DETAILED DESCRIPTION

The present disclosure provides a beaded product comprising a plurality of beads configured for oral use, and a process for the preparation thereof. Specifically, some embodiments of the present disclosure provide a beaded product comprising a plurality of beads configured for oral use, the plurality of beads comprising: from about 0.1 to about 25% by weight of a bleached plant material, based on the total weight of the beads; at least about 10% by weight of a filler, based on the total weight of the beads; at least about 0.25% by weight of a binder, based on the total weight of the beads; up to about 60% by weight of water, based on the total weight of the beads; and at least one flavoring agent, active ingredient, or a combination thereof.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements.

As used in this specification and the claims, the singular forms "a," "an," and "the" include plural referents unless the context clearly dictates otherwise.

Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

The present disclosure is generally directed to a beaded product comprising a plurality of beads, pouched products including such beads, and a process for making the beads, each of which is described herein below.

Beads

As used herein, the term "beads" is meant to include discrete small units or pieces having a generally spherical shape. The beads are generally uniform in composition, such that each bead in the plurality of beads comprises the same components and in approximately the same amounts within normal variations expected in combining and mixing the individual components. The size of the beads may vary according to the desired properties. In some embodiments, the beads have a size ranging from about 1 to about 10 mm in diameter, for example from about 1, about 2, about 3, about 4, or about 5, to about 6, about 7, about 8, about 9, or about 10 mm. Without wishing to be bound by theory, it is believed that beads having this range of sizes may be advantageous with respect to processing properties (e.g., flowability), particularly in pouched embodiments. In some embodiments, the beads have a diameter of from about 1 to about 5 mm in diameter. In some embodiments, the beads have a diameter of from about 3 to about 5 mm in diameter. In some embodiments, the beads have a diameter of from about 3 to about 10 mm in diameter.

In some embodiments, the beads can be characterized as lightened in color (e.g., "whitened") in comparison to beads prepared from an unbleached plant material. In some embodiments, the beads can be characterized as white. By "white" is meant that the beads have a whiteness value of greater than about 40 when determined according to the Commission Internationale de l'Eclairage (CIE) model as discussed herein below with respect to bleached plant materials. In some embodiments, the whiteness value is from about 42 to about 60.

The beads as disclosed herein comprise a bleached plant material, water, a filler, a binder, and at least one active ingredient, flavor, or combination thereof. The relative amounts of the various components (e.g., bleached plant material, water, filler, binder, active ingredient, flavor, and the like) within the composition may vary, and typically are selected so as to provide the desired sensory and performance characteristics to the beads. The example individual components of the beads are described herein below.

Bleached Plant Material

The beads as disclosed herein comprise a bleached plant material. By "bleached plant material" is meant a plant material, which, in its natural state possesses a color, and which has been treated to reduce or eliminate the color. By "color" is meant the characteristic of human visual perception described through color categories, with names such as red, blue, yellow (primary colors) or brown, orange, green, purple, and the like, resulting from combinations of primary colors. This perception of color derives from the stimulation of cone cells in the human eye by electromagnetic radiation in the visible spectrum, associated with objects through the wavelength of the light that is reflected from them. This reflection is governed by the object's physical properties such as e.g., absorption and emission spectra across the electromagnetic spectrum.

Certain plant materials, by virtue of naturally occurring chemical compounds therein which reflect light in the visible range of the electromagnetic spectrum, impart a color to the plant material (e.g., chlorophyll or pigment decomposition products in certain botanical materials, responsible for green color and brown colors, respectively). Such chemical compounds, or a portion thereof, which are responsible for the color of the plant material, may be chemically altered or removed by various treatments. Such a bleached plant material may be desirable e.g., to prevent tooth discoloration during use of the product including such material, to avoid discoloration of the pouch (e.g., fleece material) in a pouched product, or so that any residue remaining in the mouth of the user after use of the product is less visible, and is less likely to cause staining of fibrous materials, such as clothing, that may contact the residue.

Tobacco pulp, as well as other botanical materials, can be bleached (whitened) according to any means known in the art, and as described herein below. In some embodiments, the treatment for bleaching (i.e., altering or removing colored chemical compounds) includes extraction, chemical bleaching, or a combination thereof. One suitable extraction method is supercritical carbon dioxide ($CO_2$) extraction. Methods of chemical bleaching of e.g., botanical materials, including tobacco, are known, and include as non-limiting examples, treatment with hydrogen peroxide, ozone, or other oxidizing agents. For example, bleached botanical or tobacco material may be produced by various whitening methods using various bleaching or oxidizing agents. Example oxidizing agents include peroxides (e.g., hydrogen peroxide), chlorite salts, chlorate salts, perchlorate salts, hypochlorite salts, ozone, ammonia, potassium permanganate, and combinations thereof. Oxidation catalysts can be used. Example oxidation catalysts are titanium dioxide, manganese dioxide, and combinations thereof.

Methods of bleaching known for bleaching tobacco may be applied to other botanical materials. Processes for treating tobacco with bleaching agents are discussed, for example, in U.S. Pat. No. 787,611 to Daniels, Jr.; U.S. Pat. No. 1,086, 306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in U.S. Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference. A particularly suitable method is disclosed in, for example, U.S. patent Application Ser. No. 16/567,822, incorporated by reference herein in its entirety. Other whitening methods using reagents such as ozone and potassium permanganate can also be used. See, for example, U.S. Pat. No. 3,943,940 to Minami, which is incorporated herein by reference.

In some embodiments, the bleaching is effective to eliminate at least 70% of the chemicals present in the tobacco or botanical material having maximum transmission of wavelengths in the visible range of the electromagnetic spectrum, based on the weight of the naturally occurring compounds. For example, such treatment may be effective to remove 70%, 80%, 90%, 95%, 99%, or even 100% of the naturally occurring compounds responsible for the visible color of the plant material. Accordingly, such bleached plant materials are visually lighter in color relative to an unbleached plant material.

In some embodiments, the bleached plant material can be characterized as lightened in color (e.g., "whitened") in comparison to an untreated plant material. White colors are often defined with reference to the International Commission on Illumination's (CIE's) chromaticity diagram. The bleached plant material, can, in certain embodiments, be characterized as closer on the chromaticity diagram to pure white than an untreated plant material.

Whiteness values of bleached plant material may be determined according to the Commission Internationale de l'Eclairage (CIE) model, for example, with a hand-held color meter, relative to a control product (See "Precise Color Communication; Color Control from Perception to Instrumentation," Konica Minolta, 2007; http://konicaminolta.com/instruments/about/network, which is incorporated herein by reference). Discoloration from white may be evaluated by the E313 Whiteness Index according to ASTM method E313, using the formula WI=(3.388Z-3Y, where Y and Z are the CIE tri-stimulus values, and measured by a hand-held meter. The bleached plant material can, in certain embodiments, be characterized as closer on the chromaticity diagram to pure white than unbleached plant material.

Whiteness of a material can also be characterized based on ASTM E313-73 Whiteness Test. The whiteness of a bleached plant material can be in the range of about 1-30, 5-25, 10-20, or 10-15, for example. In some embodiments, the whiteness of a bleached plant material can be at least about 5, at least about 10, at least about 12, at least about 15, at least about 20, or at least about 25.

In some embodiments, the bleached plant material can have an ISO brightness of at least about 50%, at least about 60%, at least about 65%, at least about 70%, at least about 75%, or at least about 80%. In some embodiments, the bleached plant material can have an ISO brightness in the range of about 50% to about 90%, about 55% to about 75%, or about 60% to about 70%. ISO brightness can be measured according to ISO 3688:1999 or ISO 2470-1:2016.

Typical inclusion ranges for bleached plant materials can vary depending on the nature and type of the bleached plant material, and the intended effect on the beads, with an example range of up to about 80% by weight, such as from about 0.1% to about 80% by weight, based on total weight of the beads. In some embodiments, the beads comprise less than about 10%, or less than about 8%, or less than about 6% bleached plant material by weight. In some embodiments, the beads comprise from about 0.1, about 0.5, or about 1%, to about 5%, about 6%, about 8%, about 10%, about 12%, about 14%, about 16%, about 18%, about 20%, or about 25% bleached plant material by weight.

Non-Tobacco Botanical

In some embodiments, the bleached plant material comprises a non-tobacco botanical. As used herein, the term "botanical" refers to any plant material, including plant material in its natural form and plant material derived from natural plant materials, such as extracts or isolates from plant materials or treated plant materials (e.g., plant materials subjected to heat treatment, fermentation, or other treatment processes capable of altering the physical and/or chemical nature of the material). Reference to botanical material as "non-tobacco" is intended to exclude tobacco materials (i.e., does not include any *Nicotiana* species). The botanical materials useful in the present disclosure may comprise plant-derived non-tobacco materials, including, but not limited to, hemp, flax, sisal, rice straw, and esparto. The botanical materials useful in the present disclosure may comprise, without limitation, any of the compounds and sources set forth herein, including mixtures thereof.

Tobacco Material

In some embodiments, the bleached plant material comprises a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis subsp. Hersperis, N. pauciflora, N. petunioides, N. quadrivalvis, N. repanda, N. rotundifolia, N. solanifolia*, and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within the beads as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises lamina, stems, or a combination thereof. In certain embodiments, the tobacco material can include tobacco stems. As used herein, "stem" refers to the long thing part of a tobacco plant from which leaves or flowers grow, and can include the leaves, lamina, and/or flowers. In some embodiments, the tobacco material comprises tobacco leaf (lamina).

The beads disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina). In certain embodiments, the tobacco material comprises solid tobacco material selected from the group consisting of lamina and stems. The tobacco that is used may include tobacco lamina, or a tobacco lamina and stem mixture (of which at least a portion is smoke-treated). Portions of the tobaccos may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the tobacco material optionally may incorporate tobacco that has been fermented. See, also, the types of tobacco processing techniques set forth in International Patent Application Publication No. WO2005/063060 to Atchley et al., which is incorporated herein by reference.

In some embodiments, it can be advantageous to use stalks and/or roots of the tobacco plant. The tobacco stalks and/or roots can be separated into individual pieces (e.g., roots separated from stalks, and/or root parts separated from each other, such as big root, mid root, and small root parts) or the stalks and roots may be combined. In some embodiments, the tobacco material can comprise at least about 90% by weight roots, stalks, or a combination thereof. By "stalk" is meant the stalk that is left after the leaf (including stem and lamina) has been removed. "Root" and various specific root parts useful according to the present invention may be defined and classified as described, for example, in Mauseth, Botany: An Introduction to Plant Biology: Fourth Edition, Jones and Bartlett Publishers (2009) and Glimn-Lacy et al., Botany Illustrated, Second Edition, Springer (2006), which are incorporated herein by reference. The harvested stalks and/or roots are typically cleaned, ground, and dried to produce a material that can be described as particulate (i.e., shredded, pulverized, ground, granulated, or powdered). As used herein, stalks and/or roots can also refer to stalks and/or roots that have undergone an extraction process to remove water soluble materials. The cellulosic material (i.e., tobacco solids material) remaining after stalks and/or root materials undergo an extraction process can also be useful in the present disclosure.

For the preparation of beads, the tobacco material (e.g., a harvested plant of the *Nicotiana* species) may be subjected to a curing process. Generally, the bleached tobacco materials for inclusion within beads as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.,* 21, 305-320 (2005) and Staaf et al., *Beitrage Tabakforsch. Int.,* 21, 321-330 (2005), which are incorporated herein by reference. Certain types of tobaccos can be subjected to alternative types of curing processes, such as fire curing or sun curing.

In certain embodiments, bleached tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos and various blends of any of the foregoing tobaccos.

The bleached tobacco material may incorporate a single type of tobacco (e.g., in a so-called "straight grade" form). For example, the tobacco material may be composed solely of flue-cured tobacco (e.g., all of the tobacco may be composed, or derived from, either flue-cured tobacco lamina or a mixture of flue-cured tobacco lamina and flue-cured tobacco stem). In one embodiment, the tobacco comprises or is composed solely of sun-cured, milled *Rustica* (i.e., *N. rustica*). In one embodiment, the tobacco comprises or is composed solely of sun-cured, milled *Rustica* stems (i.e., *N. rustica* stems).

The bleached tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the beads of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or 0% by weight of tobacco material. In some embodiments, the beads of the disclosure can be characterized as completely free or substantially free of unbleached tobacco material. For example, certain embodiments can be characterized as having less than 1% by weight, or less than 0.5% by weight, or less than 0.1% by weight of unbleached tobacco material, or 0% by weight of unbleached tobacco material.

Bleached Plant Material Particle Size

The bleached plant material is typically used in a form that can be described as particulate (i.e., shredded, ground, granulated, or powder form). As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 μm, such as 500 μm, such as 400 μm, such as 300 μm.

Typically, the bleached plant material particles are sized to pass through a screen of about 18 or 16 U.S. sieve size, generally are sized to pass a screen of about 20 U.S. sieve size, often are sized to pass through a screen of about 50 U.S. sieve size, frequently are sized to pass through a screen of about 60 U.S. sieve size, may even be sized to pass through a screen of 100 U.S. sieve size, and further may be sized so as to pass through a screen of 200 U.S. sieve size. It is noted that two scales commonly used to classify particle sizes are the U.S. Sieve Series and Tyler Equivalent. Sometimes these two scales are referred to as Tyler Mesh Size or Tyler Standard Sieve Series. U.S. sieve size is referred to in the present application. If desired, air classification equipment may be used to ensure that small sized particles of the desired sizes, or range of sizes, may be collected. In one embodiment, the bleached plant material is in particulate form sized to pass through an 18 or 16 U.S. sieve size, but not through a 60 U.S. sieve size.

In certain embodiments, the bleached plant material is provided with an average particle size of about 0.05 to about 2 mm, about 0.5 to about 1.5 mm, about 0.2 to about 1.0 mm, or about 0.75 to about 1.25 mm (e.g., about 1 mm). In some embodiments, the bleached plant material is employed in particulate form, the particles having an average particle size between 1 millimeter and 50 microns.

In some embodiments, the bleached plant material characterized as being in particulate form may have at least 50% by weight of particles with a particle size as measured by sieve analysis of no greater than about 1000 μm, such as no greater than about 500 μm, such as no greater than about 400 μm, such as no greater than about 350 μm, such as no greater than about 300 μm. In some embodiments, at least 60% by weight of the particles have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 70% by weight of the particles referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 80% by weight of the particles referenced herein have a particle size as measured by sieve analysis of no greater than about 500 μm, such as no greater than about 400 μm, such as no greater than about 350 μm, such as no greater than about 300 μm. In some embodiments, at least 90% by weight of the particles referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 95% by weight of the particles referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 99% by weight of the particles referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, approximately 100% by weight of the particles referenced herein have a particle size as measured by sieve analysis of no greater than about 1000 μm, such as no greater than about 500 μm, such as no greater than about 400 μm, such as no greater than about 350 μm, such as no greater than about 300 μm.

In some embodiments, at least 50% by weight, such as at least 60% by weight, such as at least 70% by weight, such as at least 80% by weight, such as at least 90% by weight, such as at least 95% by weight, such as at least 99% by weight of the particles referenced herein have a particle size as measured by sieve analysis of from about 0.05 μm to about 1000 μm, such as from about 0.05 μm to about 750 μm, such as from about 0.1 μm to about 500 μm, such as from about 0.25 μm to about 500 μm. In some embodiments, at least 50% by weight, such as at least 60% by weight, such as at least 70% by weight, such as at least 80% by weight, such as at least 90% by weight, such as at least 95% by weight, such as at least 99% by weight of the particles referenced herein have a particle size as measured by sieve analysis of from about 10 μm to about 400 μm, such as from about 50 μm to about 350 μm, such as from about 100 μm to about 350 μm, such as from about 200 μm to about 300 μm.

Filler

The beads of some embodiments comprise a filler. Such fillers may fulfill multiple functions, such as enhancing certain organoleptic properties such as texture and mouthfeel, enhancing cohesiveness or compressibility of the beads, and the like. Generally, the fillers are porous particulate materials and are cellulose-based. For example, suitable fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential fillers include maltodextrin, dextrose, calcium carbonate, calcium phosphate, lactose, mannitol, xylitol, and sorbitol. Combinations of fillers can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the beads based on the ability of the starch material to impart a specific organoleptic property to the beads. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, and starch sodium octenyl succinate.

In some embodiments, the filler is a cellulose material or a cellulose derivative. One particularly suitable filler for use in the beads described herein is microcrystalline cellulose ("mcc"). The mcc may be synthetic or semi-synthetic, or it may be obtained entirely from natural celluloses. The mcc may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof.

The amount of filler can vary, but is typically greater than about 10%, and up to about 75% of the beads by weight, based on the total weight of the composition. A typical range of filler within the beads can be from about 10 to about 75% by total weight of the beads, for example, from about 10, about 20, about 25, or about 30, to about 35, about 40, about 45, about 50%, or about 60% by weight (e.g., about 20 to about 50%, or about 25 to about 45% by weight).

In certain embodiments, the amount of filler is at least about 10% by weight, such as at least about 20%, or at least about 30%, or at least about 35%, or at least about 40%, based on the total weight of the beads.

In some embodiments, the filler content may be described relative to the bleached plant material, wherein the weight of the filler is greater than weight of the bleached plant material.

For example, in some embodiments, the weight of the filler is at least twice the weight of bleached plant material. In some embodiments, the weight of the filler is from about 2 to about 100 times the weight of bleached plant material, such as from about 5 to about 50, or from about 10 to about 20 times the weight of bleached plant material.

Binder

The beads of some embodiments comprise a binder (or combination of binders) in amounts sufficient to provide the desired physical attributes and physical integrity to the beads. The amount of binder utilized in the beads can vary based on the binder and the desired bead properties, but is typically at least about 0.25%, and often up to about 5% by weight. Certain embodiments are characterized by a binder content of at least about 1% by weight, such as about 1 to about 5% by weight, or about 1 to about 3% by weight, based on the total weight of the bead.

Typical binders can be organic or inorganic, or a combination thereof. Representative binders include cellulose ethers, povidone, sodium alginate, starch-based binders, gums, pectin, carrageenan, pullulan, zein, and the like, and combinations thereof. In certain embodiments, the binder comprises a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. In some embodiments, the binder comprises a cellulose ether.

In some embodiment, the binder comprises a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose ethers include methylcellulose, hydroxypropylcellulose ("HPC"), hydroxypropylmethylcellulose ("HPMC"), hydroxyethyl cellulose, and carboxymethylcellulose ("CMC"). In one embodiment, the binder is one or more of methylcellulose, HPC, HPMC, hydroxyethyl cellulose, and CMC. In some embodiments, the binder is CMC. In some embodiments, the beads comprise from about 1 to about 5% by weight of CMC, for example, from about 1%, about 2%, or about 3%, to about 4%, or about 5% by weight of the beads.

Water

The moisture content (e.g., water content) of the beads, prior to use by a consumer, may vary according to the desired properties. Typically, the beads, as present within e.g., a pouched product, prior to insertion into the mouth of the user, is up to about 60% by weight of water, and is generally from about 5 to about 55% by weight of water, for example, from about 5 to about 55%, or from 10 to about 50%, from about 20 to about 45%, or from about 25 to about 40% water by weight. In some embodiments, the beads comprise from about 5 to about 25% water by weight, based on the total weight of the beads.

Flavoring Agent

In some embodiments, the beads comprise one or more flavoring agents. As used herein, a "flavoring agent" or "flavorant" is any flavorful or aromatic substance capable of altering the sensory characteristics associated with the beads. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, eucalyptus, lavender, cardamon, nutmeg, cinnamon, clove, cascarilla, sandalwood, honey, jasmine, ginger, anise, sage, licorice, lemon, orange, apple, peach, lime, cherry, strawberry, trigeminal sensates, terpenes and any combinations thereof. See also, Leffingwell et al., Tobacco Flavoring for Smoking Products, R. J. Reynolds Tobacco Company (1972), which is incorporated herein by reference. flavoring agents also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The amount of flavoring agent utilized in the beads can vary, but is typically up to about 10% by weight, and certain embodiments are characterized by a flavoring agent content of at least about 0.1% by weight, such as about 0.5 to about 10%, about 1 to about 5%, or about 2 to about 4% weight, based on the total weight of the beads.

Active Ingredient

In some embodiments, the beads include one or more active ingredients. As used herein, an "active ingredient" refers to one or more substances belonging to any of the following categories: API (active pharmaceutical substances), food additives, herbal materials, natural medicaments, and naturally occurring substances that can have an effect on humans. Example active ingredients include any ingredient known to impact one or more biological functions within the body, such as ingredients that furnish pharmacological activity or other direct effect in the diagnosis. cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., herbal materials) that provide one or more advantageous biological effects (e.g., health promotion, disease prevention, or other medicinal properties), but are not classified or regulated as drugs.

Non-limiting examples of active ingredients include those falling in the categories of herbal materials, stimulants, amino acids, vitamins, antioxidants, nicotine components, pharmaceutical ingredients (e.g., nutraceutical and medicinal ingredients), and cannabinoids. Each of these categories is further described herein below. The particular choice of active ingredients will vary depending upon the desired flavor, texture, and desired characteristics of the particular product.

The particular percentages of active ingredients present will vary depending upon the desired characteristics of the particular product. Typically, an active ingredient or combination thereof is present in a total concentration of at least about 0.001% by weight of the beads, such as in a range from about 0.001% to about 20%. In some embodiments, the active ingredient or combination of active ingredients is present in a concentration from about 0.1% w/w to about 10% by weight, such as, e.g., from about from about 0.5% w/w to about 10%, from about 1% to about 10%, from about 1% to about 5% by weight, based on the total weight of the beads. In some embodiments, the active ingredient or combination of active ingredients is present in a concentration of from about 0.001%, about 0.01%, about 0.1%, or about 1%, up to about 20% by weight, such as, e.g., from about from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the beads. Further suitable ranges for specific active ingredients are provided herein below.

Herbal Materials

In some embodiments, the active ingredient comprises one or more herbal materials. For the purposes of the present disclosure, the term "herbal materials" refers to seed-producing plants that do not develop persistent woody tissue and are often valued for their medicinal or sensory characteristics (e.g., teas or tisanes). Certain herbal materials, as the plant material or an extract thereof, have found use in traditional herbal medicine. Non-limiting examples of herbal materials or herbal-derived materials include hemp, eucalyptus, rooibos, fennel, citrus, cloves, lavender, peppermint, chamomile, basil, rosemary, ginger, turmeric, green tea, white mulberry, cannabis, cocoa, ashwagandha, baobab, chlorophyll, cordyceps, damiana, ginseng, guarana, and maca.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis.

When present, a stimulant or combination of stimulants (e.g., caffeine, theacrine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the beads.

Amino Acids

In some embodiments, the active ingredient comprises an amino acid. As used herein, the term "amino acid" refers to an organic compound that contains amine (—NH$_2$) and carboxyl (—COOH) or sulfonic acid (SO$_3$H) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-translational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine.

When present, an amino acid or combination of amino acids is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the beads.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones).

When present, a vitamin or combination of vitamins (e.g., vitamin B6, vitamin B12, vitamin E, vitamin C, or a combination thereof) is typically at a concentration of from about 0.01% w/w to about 1% by weight, such as, e.g., from about from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, or about 1% by weight, based on the total weight of the beads.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical/herbal materials. Non-limiting examples of antioxidants include certain botanical/herbal materials, vitamins, polyphenols, and phenol derivatives.

Examples of botanical/herbal materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, withania somnifera, Lion's mane, and silybum marianum. Such herbal materials may be provided in fresh or dry form, essential oils, or may be in the form of an extracts. The herbal materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof. In some embodiments, the antioxidant is Vitamin E or a derivative thereof, a flavonoid, a polyphenol, a carotenoid, or a combination thereof.

When present, an antioxidant is typically at a concentration of from about 0.001% w/w to about 10% by weight, such as, e.g., from about from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the beads.

Nicotine Component

In certain embodiments, the active ingredient comprises a nicotine component. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, Beitrage Tabakforschung Int., 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the composition, such as in a range from about 0.001% to about 10%. In some embodiments, the nicotine component is present in a concentration from about 0.1% w/w to about 10% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about from about 0.1% w/w to about 2.5%, from about 0.1% to about 2.0%, from about 0.1% to about 1.5%, or from about 0.1% to about 1% by weight, calculated as the free base and based on the total weight of the composition. In some embodiments, the active ingredient comprises a nicotine component (e.g., beads of the disclosure, in addition to comprising any active ingredient or combination of active ingredients as disclosed herein, may further comprise a nicotine component).

In some embodiments, the beads of the disclosure can be characterized as completely free or substantially free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical or herbal material. For example, certain embodiments can be characterized as having less than 0.001% by weight of nicotine, or less than 0.0001%, or even 0% by weight of nicotine, calculated as the free base.

Cannabinoids

In some embodiments, the active ingredient comprises one or more cannabinoids. As used herein, the term "cannabinoid" refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in cannabis; and synthetic cannabinoids, manufactured artificially. Non-limiting examples of cannabinoids include tetrahydrocannabinol (THC), the primary psychoactive compound in cannabis, and cannabidiol (CBD) another major constituent of the plant, but which is devoid of psychoactivity. In some embodiments, the active ingredient comprises CBD.

When present, a cannabinoid (e.g., CBD) is typically in a concentration of at least about 0.1% by weight of the beads, such as in a range from about 0.1% to about 30%, such as, e.g., from about from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the beads.

Pharmaceutical Ingredients

In some embodiments, the active ingredient comprises one or more pharmaceutical ingredients. The pharmaceutical ingredient can be any known agent adapted for therapeutic, prophylactic, or diagnostic use. These can include, for example, synthetic organic compounds, proteins and peptides, polysaccharides and other sugars, lipids, inorganic compounds, and nucleic acid sequences, having therapeutic, prophylactic, or diagnostic activity. Non-limiting examples of pharmaceutical ingredients include analgesics and antipyretics (e.g., acetylsalicylic acid, acetaminophen, 3-(4-isobutylphenyl)propanoic acid).

Salts

In some embodiments, the beads comprise a salt (e.g., an alkali metal salt), typically employed in an amount sufficient to provide desired sensory attributes to the beads. Non-limiting examples of suitable salts include sodium chloride, potassium chloride, ammonium chloride, flour salt, sodium acetate, sodium citrate, and the like. In some embodiments, the salt is sodium chloride, ammonium chloride, or a combination thereof.

When present, a representative amount of salt is about 0.5% by weight or more, about 1.0% by weight or more, or about 1.5% by weight or more, but will typically make up about 10% or less of the total weight of the beads, or about 7.5% or less, or about 5% or less (e.g., from about 2 to about 6% by weight, or from about 0.5 to about 5% by weight).

Sweeteners

In order to improve the sensory properties of the beads according to the disclosure, one or more sweeteners may be added. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, stevia, honey, and the like. Examples of artificial sweeteners include sucralose, isomaltulose, maltodextrin, saccharin, aspartame, acesulfame K, neotame, and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the sweetener is xylitol, sucralose, or a combination thereof.

When present, a sweetener or combination of sweeteners may make up from about 0.1 to about 20% or more of the of the beads by weight, for example, from about 0.1 to about 1%, from about 1 to about 5%, from about 5 to about 10%, or from about 10 to about 20% by weight, based on the total weight of the composition. In some embodiments, a combination of sweeteners is present at a concentration of from about 1% to about 3% by weight of the beads.

Taste Modifiers

In order to improve the organoleptic properties of the beads as disclosed herein, the beads may include one or more taste modifying agents ("taste modifiers") which may serve to mask, alter, block, or improve e.g., the flavor of the beads as described herein. Non-limiting examples of such taste modifiers include analgesic or anesthetic herbs, spices, and flavors which produce a perceived cooling (e.g., menthol, eucalyptus, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the composition comprises an active ingredient having a bitter taste, and a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., an active ingredient). In some embodiments, the taste modifier is capsaicin.

In some embodiments, the taste modifier is the amino acid gamma-amino butyric acid (GABA), referenced herein above with respect to amino acids. Studies in mice suggest that GABA may serve function(s) in taste buds in addition to synaptic inhibition. See, e.g., Dvoryanchikov et al., J Neurosci. 2011 Apr. 13; 31(15):5782-91. Without wishing to be bound by theory, GABA may suppress the perception of certain tastes, such as bitterness. In some embodiments, the composition comprises caffeine and GABA.

In some embodiments, the taste modifier is adenosine monophosphate (AMP). AMP is a naturally occurring nucleotide substance which can block bitter food flavors or enhance sweetness. It does not directly alter the bitter flavor, but may alter human perception of "bitter" by blocking the associated receptor.

In some embodiments, the taste modifier is lactisole. Lactisole is an antagonist of sweet taste receptors. Temporarily blocking sweetness receptors may accentuate e.g., savory notes.

When present, a representative amount of taste modifier is about 0.01% by weight or more, about 0.1% by weight or more, or about 1.0% by weight or more, but will typically make up less than about 10% by weight of the total weight of the beads, (e.g., from about 0.01%, about 0.05%, about 0.1%, or about 0.5%, to about 1%, about 5%, or about 10% by weight of the total weight of the beads).

Buffering Agents

In certain embodiments, the beads of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Non-limiting examples of suitable buffers include alkali metals acetates, glycinates, phosphates, glycerophosphates, citrates, carbonates, hydrogen carbonates, borates, or mixtures thereof. In some embodiments, the buffer is sodium bicarbonate.

Where present, the buffering agent is typically present in an amount less than about 5% by weight, based on the weight of the beads, for example, from about 0.1% to about 5%, such as, e.g., from about 0.1% to about 1%, or from about 0.1% to about 0.5% by weight, based on the total weight of the beads.

Colorants

A colorant may be employed in amounts sufficient to provide the desired physical attributes to the beads. Examples of colorants include various dyes and pigments, such as caramel coloring and titanium dioxide. The amount of colorant utilized in the beads can vary, but when present is typically up to about 3% by weight, such as from about 0.1%, about 0.5%, or about 1%, to about 3% by weight, based on the total weight of the beads.

Humectants

In certain embodiments, one or more humectants may be employed in the beads. Examples of humectants include, but are not limited to, glycerin, propylene glycol, and the like. Where included, the humectant is typically provided in an amount sufficient to provide desired moisture attributes to the beads. Further, in some instances, the humectant may impart desirable flow characteristics. In some embodiments, the humectant is glycerin, propylene glycol, or a combination thereof.

When present, a humectant will typically make up about 5% or less of the weight of the beads (e.g., from about 0.1 to about 5% by weight), for example, from about 0.1% to about 1% by weight, or about 1% to about 5% by weight, based on the total weight of the beads.

Oral Care Additives

In some embodiments, the beads comprise an oral care ingredient (or mixture of such ingredients). Oral care ingredients provide the ability to inhibit tooth decay or loss, inhibit gum disease, relieve mouth pain, whiten teeth, or otherwise inhibit tooth staining, elicit salivary stimulation, inhibit breath malodor, freshen breath, or the like. For example, effective amounts of ingredients such as thyme oil, eucalyptus oil and zinc (e.g., such as the ingredients of formulations commercially available as ZYTEX® from Discus Dental) can be incorporated into the composition. Other examples of ingredients that can be incorporated in desired effective amounts within the present beads can include those that are incorporated within the types of oral care compositions set forth in Takahashi et al., Oral Microbiology and Immunology, 19(1), 61-64 (2004); U.S. Pat. No. 6,083,527 to Thistle; and US Pat. Appl. Pub. Nos. 2006/0210488 to Jakubowski and 2006/02228308 to Cummins et al. Other example ingredients for oral care include those contained in formulations marketed as MALTISORB® by Roquette and DENTIZYME® by NatraRx. When present, a representative amount of oral care additive is at least about 1%, often at least about 3%, and frequently at least about 5% of the total dry weight of the beads. The amount of oral care additive within the beads will not typically exceed about 30%, often will not exceed about 25%, and frequently will not exceed about 20%, of the total dry weight of the beads.

Other Additives

Other additives can be included in the disclosed beads. For example, the beads can be processed, blended, formulated, combined, and/or mixed with other materials or ingredients. The additives can be artificial, or can be obtained or derived from herbal or biological sources. Examples of further types of additives include thickening or gelling agents (e.g., fish gelatin), emulsifiers, preservatives (e.g., potassium sorbate and the like), disintegration aids, or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the beads, with an example range of up to about 10% by weight, based on total weight of the beads (e.g., about 0.1 to about 5% by weight).

The aforementioned additives can be employed together (e.g., as additive formulations) or separately (e.g., individual additive components can be added at different stages involved in the preparation of the final composition). Furthermore, the aforementioned types of additives may be encapsulated as provided in the final product or composition. Example encapsulated additives are described, for example, in WO2010/132444 to Atchley, which has been previously incorporated by reference herein.

Configured for Oral Use

Certain embodiments of the disclosure provide a beaded product comprising a plurality of beads configured for oral use. The term "configured for oral use" as used herein means that the beads are provided in a form such that during use, saliva in the mouth of the user causes one or more of the components of the beads (e.g., flavoring agents and/or active ingredients) to pass into the mouth of the user. In certain embodiments, the beads are adapted to deliver components to a user through mucous membranes in the user's mouth, the user's digestive system, or both, and, in some instances, said component is an active ingredient (including, but not limited to, for example, a nicotine component, a flavor, a stimulant, vitamin, taste modifier, or combination thereof) that can be absorbed through the mucous membranes in the mouth or absorbed through the digestive tract when the beads are used.

In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The beads of the present disclosure may be dissolvable. As used herein, the terms "dissolve," "dissolving," and "dissolvable" refer to beads having aqueous-soluble components that interact with moisture in the oral cavity and enter into solution, thereby causing gradual consumption of the beads. According to one aspect, the dissolvable beads are capable of lasting in the user's mouth for a given period of time until it completely dissolves. Dissolution rates can vary over a wide range, from about 1 minute or less to about 60 minutes. For example, fast release compositions typically dissolve and/or release the active substance in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the beads. In other embodiments, the products do not dissolve during the product's residence in the user's mouth.

In some example embodiments, the beads of the present disclosure are disposed within a moisture-permeable container (e.g., a water-permeable pouch) to form a pouched product. Such products in the water-permeable pouch format are typically used by placing one pouch containing the beads in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the beads therein (e.g., flavoring agents and/or active ingredients) to pass through e.g., the water-permeable pouch and provide the user with flavor and satisfaction, and the user is not required to spit out any portion of the composition. After about 10 minutes to about 60 minutes, typically about 15 minutes to about 45 minutes, of use/enjoyment, substantial amounts of the composition have been absorbed through oral mucosa of the human subject, and the pouch may be removed from the mouth of the human subject for disposal.

Accordingly, in certain embodiments, the beads as disclosed herein are combined within a moisture-permeable packet or pouch that acts as a container for use of the composition to provide a pouched product configured for oral use. Certain embodiments of the disclosure will be described with reference to FIG. 1 of the accompanying drawings, and these described embodiments involve snus-type products having an outer pouch and containing beads as described herein. As explained in greater detail below, such embodiments are provided by way of example only, and the pouched products of the present disclosure can include the beads in other forms. The composition/construction of such packets or pouches, such as the container pouch 102 in the embodiment illustrated in FIG. 1, may be varied. Referring to FIG. 1, there is shown a first embodiment of a pouched product 100. The example pouched product 100 includes a moisture-permeable container in the form of a pouch 102, which contains a plurality of beads 104 as described herein.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The beads may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the beads readily diffuse through the pouch and into the mouth of the user.

Non-limiting examples of suitable types of pouches are set forth in, for example, U.S. Pat. No. 5,167,244 to Kjerstad and U.S. Pat. No. 8,931,493 to Sebastian et al.; as well as U.S. Patent App. Pub. Nos. 2016/0000140 to Sebastian et al.; 2016/0073689 to Sebastian et al.; 2016/0157515 to Chapman et al.; and 2016/0192703 to Sebastian et al., each of which is incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and beads each may undergo complete dispersion within the mouth of the user during normal conditions of use, and hence the pouch and beads both may be ingested by the user. Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the bead contents permeate through the pouch material prior to the time that the pouch undergoes loss of its physical integrity. If desired, flavoring ingredients, disintegration aids, and other desired components, may be incorporated within, or applied to, the pouch material.

The quantity of the beads contained within each product unit, for example, a pouch, may vary. In some embodiments, the weight of the beads within each pouch is at least about 50 mg, for example, from about 50 mg to about 1 gram, from about 100 to 800 about mg, or from about 200 to about 700 mg. In some smaller embodiments, the weight of the beads within each pouch may be from about 100 to about 300 mg. For a larger embodiment, the weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference. In some embodiments, the pouched product contains only the beads as disclosed herein (i.e., no additional components, such as tobacco materials, are enclosed within the pouch).

Some embodiments provide a pouched product comprising the beaded product (e.g., a white beaded product) as disclosed herein, enclosed in a pouch, wherein a whiteness value of the pouched product is greater than about 40 when determined according to the Commission Internationale de l'Eclairage (CIE) model. In some embodiments, the whiteness value is from about 42 to about 60.

A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., U.S. Pat. No. D592,956 to Thiellier; U.S. Pat. No. D594,154 to Patel et al.; and U.S. Pat. No. D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference.

Alternatively, beaded products according to certain embodiments of the disclosure can be used in aerosol generating segments of heat-not-burn (HNB) devices. See, for example, US Patent App. Pub. Nos. 2017/0065000 to Sears et al.; 2015/0157052 to Ademe et al.; U.S. Pat. No. 10,314,330 to Conner et al.; U.S. Pat. No. 9,345,268 to Stone et al.; U.S. Pat. No. 9,149,072 to Conner et al.; U.S. Pat. Nos. 5,105,831 and 5,042,509, both to Banerjee et al., each of which is incorporated herein by reference.

Preparation of Beads

In another aspect is provided a process for a beaded product comprising a plurality of beads as disclosed herein. As a non-limiting example description, the beads disclosed herein may be prepared by combining the individual bead components (e.g., bleached plant material, filler, binder, water, and flavorant and/or active ingredient) to form a mixture, granulating the mixture to form an agglomerate, extruding the agglomerate to form an extrudate, and spheronizing the extrudate. Each portion of the process is described further herein below.

The process comprises receiving a bleached plant material having a particle size of from about 0.05 mm to about 1 mm. The manner by which the bleached plant material is received in a finely divided or powder type of form may vary. In some embodiments, the process comprises grinding the bleached plant material to reduce the particle size. Preferably, plant parts or pieces are comminuted, ground, or pulverized into a particulate form using equipment and techniques for grinding, milling, or the like. Most preferably, the bleached plant material is relatively dry in form during grinding or milling, using equipment such as hammer mills, cutter heads, air control mills, air classifier mills, ball mills, rod mills, air impingement mills, roller mills, or the like, or any combination of mills. Bleached plant material may be ground or milled when the moisture content thereof is less than about 15% by weight, or less than about 5% by weight. In some instances, the bleached plant material particles may be sized to pass through a screen mesh to obtain the particle size range required.

The bleached plant material, water, a filler, a binder, and at least one flavoring agent, active ingredient, or a combination thereof, each as described herein above, are combined to form a mixture. The manner by which the various components (e.g., bleached plant material, binder, water, active ingredient, and the like) are combined may vary. For example, by adding the water, a binder, and at least one flavoring agent, active ingredient, or a combination thereof, to the bleached plant material. To be clear, reference to "adding" should not be construed as limiting with respect to the manner in which the various components are brought into contact with one another. For example, the components noted above, which may be in liquid or dry solid form, can be admixed in a pretreatment step prior to mixture with any remaining components, or simply mixed together with all other liquid or dry ingredients. Any individual component of the beads may be added to any other bead components, either individually or in any combination. In some embodiments, the process further comprises the addition of one or more fillers, one or more salts, one or more sweeteners, one or more humectants, one or more buffers, or combinations thereof, to form the mixture.

The various components of the beads may be contacted, combined, or mixed together using any mixing technique or equipment known in the art. Any mixing method that brings the bead ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

The mixture is then granulated (agglomerized). Granulation is the process in which the primary powder particles of the individual components are made to adhere to form large, homogenous, multiparticle entities called granules. Any suitable means for granulation may be employed. For example, granulation can be conducted under high-shear, low-shear, fluid bed, rotor, or melt granulation.

The agglomerate is then extruded. The extrusion can be carried out using extruders such as screw, sieve, basket, roll, and ram-type extruders, extruding the agglomerate through suitably sized pierced screens. Any suitable extrudate shape may be used. In some embodiments, the agglomerate is extruded into rods.

The extrudate is then processed in a spheronizer (e.g., such as spheronizers (marumerizers) available from Caleva Process Solutions Ltd. or LCI Corporation) at a suitable rotation speed (e.g., 1200 RPM) for a suitable time (e.g., 10 minutes). For example, spheronization can be carried out using a spinning friction plate that effects rounding of extrudate particles.

The beads may optionally be dried to remove at least a portion of the liquid content (e.g., water). The resulting beads may be dried in fluid bed dryers, apron dryers, rotary dryers, flash dryers, tray dryers or plow mixers. The final moisture content may be from 5-20% moisture on a wet basis. Additionally, flavorants and/or coatings can be added to the beads after drying.

Following the optional drying, the variously-sized beads can be processed through a series of screens to provide the desired size range, such as the sizes noted above (e.g., from about 1 to about 10 mm diameter).

In one embodiment, the method further comprises enclosing the beads in a pouch to form a pouched product, as described herein above.

In another aspect are provided beads prepared by the method as disclosed herein.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

Aspects of the present invention are more fully illustrated by the following examples, which are set forth to illustrate certain aspects of the present invention and are not to be construed as limiting thereof.

Example 1

Bleached Plant Material

Bleached tobacco is produced by using a process involving tobacco material extraction, and then bleaching with hydrogen peroxide. One suitable method is disclosed in U.S. patent application Ser. No. 16/567,822, previously incorporated herein by reference.

About 135 lbs. of milled Rustica stem is mixed with about 1217 lbs. of water and 0.74 lb EDTA. The slurry is agitated for about 1 hour at a temperature of 82° C. About 1.08 lb NaOH is added to the slurry. The slurry is discharged and the tobacco material is drained using a basket centrifuge.

The resulting tobacco material is subjected to a peroxide bleaching process: tobacco material is mixed with about 1177 lbs. water, 4.6 lbs. sodium hydroxide, 0.49 lbs. 40% sodium silicate solution, 0.49 lb EDTA, 179 lbs. of 30% hydrogen peroxide, and about 0.16 lb Xiameter AFE-0100 antifoam. The slurry is agitated for about 1 hour at a temperature of 85° C. The slurry is drained using a basket centrifuge. About 300 lbs. of water is used to rinse the tobacco material giving the bleached tobacco solid. The bleached tobacco solid is dried to a moisture content of about 10-15%.

Example 2

Bead Preparation (Low Tobacco)

In one embodiment, beads comprising the ingredients set forth in Table 1 below are prepared. The actual ingredients and percentages can be varied depending on the desired properties of the final product.

TABLE 1

Example bead composition (low tobacco)

| Ingredient | % by weight range |
| --- | --- |
| Bleached tobacco | 0.1-25 |
| Filler | 10-75 |
| Water | 5-60 |
| CMC (Binder) | 0.25-5 |
| Nicotine | 0.5-1.5 |
| Flavoring agent | 1-20 |
| Humectant | 0.5-20 |
| Sweetener | 1-6 |
| Sodium chloride | 2-6 |
| Buffer | 0.5-1.5 |
| Preservative | 0.5-1.5 |

The beads are prepared using the following method:

Bleached tobacco is weighed and transferred into a model FM 130 D Littleford precision plough mixer. Water, nicotine, flavorant, sweetener, salt, buffer, and preservative are added. The contents are mixed at 100 rpm for 10 min.

The mixer is stopped, and then a premade slurry of carboxymethyl cellulose is added, and the contents mixed for another 20 minutes at 100 rpm. The premade slurry is prepared by hydrating carboxymethyl cellulose with water in a vessel using a pitched fork propeller. This is carried out for 30 minutes.

After mixing for 20 minutes, the Littleford contents are portioned and transferred into a model MG-55-1 Fuji Paudel Co. Ltd. Multi-grain extruder. The mass is extruded through a 2-3 mm doomed screen die, resulting in multi-grain (hair-like) shaped rods.

The rods are subsequently transferred into a model QJ-230T-2 Fuji Paudel Co. Ltd. laboratory marumerizer. The marumerizer rotating bowl is used to reshape the rods into rounded beads. Subsequently, the beads are transferred into a model Flo-Coater Vector Corporation fluidized bed agglomerator and finally dried to 10% moisture with 60-70° C. heated air.

Example 3

Bead Preparation (High Tobacco)

In another embodiment, pouched beads comprising the ingredients set forth in Table 2 below are prepared. The actual ingredients and percentages can be varied depending on the desired properties of the final product.

TABLE 2

Example bead composition (high tobacco)

| Ingredient | % by weight range |
| --- | --- |
| Bleached tobacco | 29-80 |
| Filler (calcium carbonate) | 20-30 |
| Water | 20-30 |
| Binder | 0.5-1 |
| Flavoring agent | 0-20 |
| Humectant | 0-20 |
| Sweetener | 1-2 |
| Buffer | 0.2-1.0 |

The pouched beads are prepared using the following method:

Binder is added to flavor concentrate, with or without humectant (glycerin, propylene glycol, or a mixture thereof), and water. The combination is mixed to hydrate and form a bead solution. Separately, calcium carbonate is combined with bleached tobacco in a plough mixer. The bead solution is added and mixed. After mixing, the composition is discharged from the mixer and fed into an extruder. The extruded strands are fed into a spheronizer, dried, and screened to provide finished beads. The beads are enclosed in snus pouches.

What is claimed is:

1. A process for preparing a product comprising a plurality of beads configured for oral use, the plurality of beads comprising a bleached plant material, a binder, a filler, water, and at least one flavoring agent, active ingredient, or a combination thereof, the process comprising:
   receiving a bleached plant material having a particle size of from about 50 μm to about 1 mm;
   adding water, a filler, a binder, and at least one flavoring agent, active ingredient, or a combination thereof, to the bleached plant material to form a mixture;
   granulating the mixture to form an agglomerate;
   extruding the agglomerate to form an extrudate;
   spheronizing the extrudate to form the beads; and
   optionally, drying the beads.

2. The process of claim 1, further comprising grinding the bleached plant material to reduce the particle size prior to said adding.

3. The process of claim 1, wherein the bleached plant material comprises a tobacco material, a non-tobacco botanical material, or a combination thereof.

4. The process of claim 1, wherein the bleached plant material consists of tobacco stems, tobacco stalks, tobacco roots, extracted tobacco fiber, or a combination thereof.

5. The process of claim 1, wherein the bleached plant material comprises Rustica tobacco stems.

6. The process of claim 1, wherein the bleached plant material is substantially free of tobacco material.

7. The process of claim 1, wherein the bleached plant material is substantially free of unbleached tobacco material.

8. The process of claim 1, further comprising adding one or more salts, one or more sweeteners, one or more humectants, or combinations thereof, to the bleached plant material prior to granulating.

9. The process of claim 1, wherein the binder is selected from the group consisting of alginates, cellulose ethers, gums, dextrans, carrageenan, and combinations thereof.

10. The process of claim 1, wherein the binder is a cellulose ether selected from the group consisting of methylcellulose, hydroxyethyl cellulose, hydroxypropylcellulose (HPC), hydroxypropylmethylcellulose (HPMC), carboxymethylcellulose (CMC), and combinations thereof.

11. The process of claim 1, wherein the active ingredient comprises one or more nicotine components, stimulants, amino acids, vitamins, antioxidants, cannabinoids, nutraceuticals, pharmaceutical agents, or a combination thereof.

12. The process of claim 1, wherein the active ingredient comprises a nicotine component.

13. The process of claim 1, wherein the beads are substantially free of nicotine.

14. The process of claim 1, wherein the beads are from about 1 to about 10 mm in diameter.

15. The process of claim 1, further comprising enclosing the beads in a pouch to form a pouched product.

* * * * *